United States Patent [19]

Petree et al.

[11] 4,130,582

[45] Dec. 19, 1978

[54] PREPARATION OF PHENOLIC ETHYLENEDIAMINEPOLYCARBOXYLIC ACIDS

[75] Inventors: Harris E. Petree, Kernersville; Hal L. Myatt, Greensboro; Alex M. Jelenevsky, Nashville, all of N.C.

[73] Assignee: Ciba-Geigy Corporation, Ardsley, N.Y.

[21] Appl. No.: 788,712

[22] Filed: Apr. 19, 1977

[51] Int. Cl.$^2$ .............................................. C07C 51/00
[52] U.S. Cl. ..................................................... 562/448
[58] Field of Search .......................................... 260/519

[56] References Cited

U.S. PATENT DOCUMENTS

| | | | |
|---|---|---|---|
| 2,824,128 | 2/1958 | Dexter ................................. | 260/519 |
| 3,825,592 | 7/1974 | McCrary et al. .................... | 260/519 |

*Primary Examiner*—James O. Thomas, Jr.
*Assistant Examiner*—James H. Reamer
*Attorney, Agent, or Firm*—Harry Falber

[57] ABSTRACT

A process for the preparation of phenolic ethylenediamine polycarboxylic acids in predominantly the ortho isomeric form which comprises reacting a phenol compound, ethylenediamine, glyoxylic acid and a base, said phenol compound functioning both as a reactant and as the sole solvent for the reaction system. The product can then be isolated or directly reacted with an iron salt to form the corresponding iron chelate.

4 Claims, No Drawings

PREPARATION OF PHENOLIC ETHYLENEDIAMINEPOLYCARBOXYLIC ACIDS

Ethylene-bis-(α-imino-o-hydroxyphenyl-acetic acid) and derivatives thereof are capable of chelating polyvalent metal ions in neutral and alkaline solutions. Extensive testing has shown these compounds to be remarkably effective in the correction of iron chlorosis in plants growing in alkaline and calcareous soils. The use of these chelating agents increases crop yields and restores sub-marginal agricultural areas to greater productivity. It has also been determined, however, that the corresponding para isomers do not exhibit similar iron chelating capabilities.

Various methods for preparing such compounds are known. One method is disclosed in U.S. Pat. No. 2,824,128 and comprises reacting, under alkaline conditions, sodium glyoxylate, ethylenediamine and phenol in an aqueous solution and in the presence of a water-miscible solvent such as methanol, ethanol or isopropanol. The use of these solvent systems is required in order to provide the capability for dissolving the various reactants and for enabling the reaction to proceed. While this procedure represents a significant improvement over previously known methods in terms of the number of chemical manipulations and the product yield, it nevertheless exhibits certain disadvantages. The primary disadvantage is noted in the fact that the reaction produces mixtures of ortho and para isomers according to the following chemical reactions

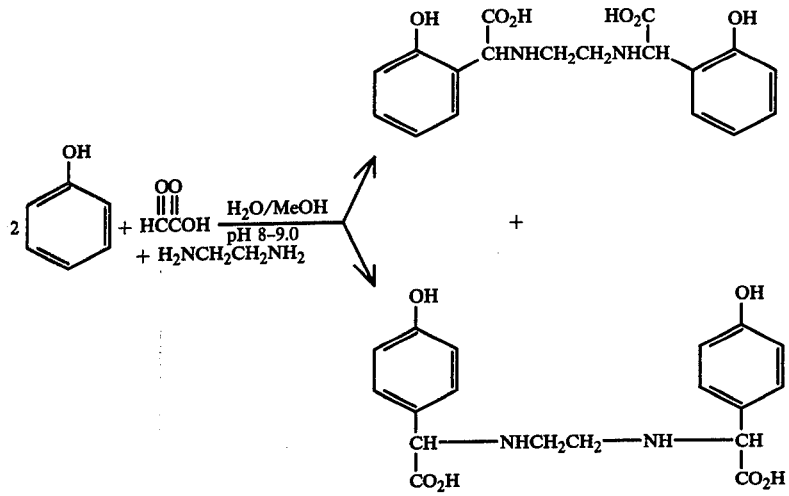

However, since the formation of the para isomer predominates (generally about 80%) in this reaction and, as previously noted, the para-substituted compound does not form a stable iron chelate under alkaline conditions, it is seen that the reaction is limited in its capability to prepare compounds which are readily utilizable as plant trace metal chelate nutrients.

In 1959, Kornblum and Lurie (J. Am. Chem. Soc., 81, 2705 (1959)) indicated the sodium salts of phenol in heterogeneous reactions exclusively carbon alkylated (ortho) rather than oxygen alkylated. In 1963, studies of Kornblum, Bereigan, and LeNoble (J. Am. Chem. Soc., 85, 9941 (1963)) demonstrated that the solvent in which an ambident anion (sodium phenoxide) reaction is conducted may decide the reaction course. The dielectric constant and the capacity for solvating ions were solvent properties Kornblum invoked as accounting for the ability of solvent to control the course of ambident anion alkylations. In the instant situation, the phenoxide ion is capable of bond formation at the oxygen or at the ortho and para ring cabon atoms.

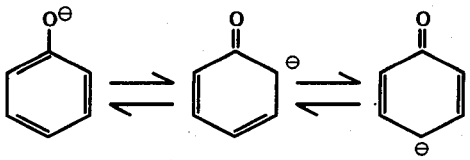

Since the formation of the instant free acid was proposed to be a Mannich type reaction, oxygen alkylation was not considered feasible; however, the active ortho or para-hydrogen atom on the phenol will condense with the glyoxylic acid and ethylenediamine. To effect ortho substitutions on phenol, a variety of solvents were employed. Most non-aqueous solvents lacked the capability of dissolving the starting reagents and therefore, no reaction took place. When water was used as a solvent, the reaction product was predominantly the para isomer. When methanol-water solvent mixtures were used, the product distribution is directed towards 80–90% of the undesired para-isomer. In addition, various phenoxide salts (U.S. Pat. No. 3,331,879) have been found to direct ortho substitution; however, most are very expensive group V-B metals.

It is, therefore, the object of this invention to provide a process for the preparation of phenolic ethylenediamine-polycarboxylic acids, which process ensures the predominant formation of the ortho-isomer.

It is a further object to provide such a process without adversely affecting the yield or quality of the resulting product.

Other objects and advantages of this invention will be readily apparent from the following detailed description thereof.

We have now, surprisingly, discovered that by utilizing phenol both as a reactant and as the sole solvent in the reaction system, the resulting phenol ethylenediaminepolycarboxylic acid product mix contains predominant amounts of the ortho-isomeric form. Thus, rather than utilizing the solvent systems of the prior art processes, excess phenol is added so that it can function both as a reactant and as the sole solvent. By relying on the ortho directing capability of phenol, generally greater than about 85% of the product mix is now represented by the ortho-substituted compound.

Accordingly, the resulting free acid can be readily and directly reacted with an iron salt to form the iron chelate under alkaline conditions, said predominantly ortho-substituted chelate being available and effective for argicultural uses.

The excess phenol also provides the necessary solubilizing capability for the reactants so as to enable the reaction to rapidly proceed. In addition, the process maintains high product purity and satisfactory yields. The novel process of this invention is typified by the following reaction sequence

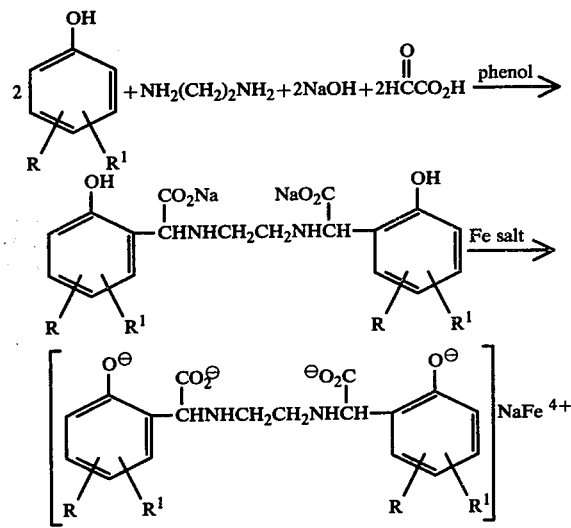

wherein R and $R^1$ are independently selected from hydrogen, methyl, ethyl, halogen, methoxy, hydroxyl, carboxyl, sulfo and acetyl. Typical compounds include phenol; o-, m-and p-cresol; o- and p-methoxyphenol; 3,4- and 2,4-dihydroxytoluene; and the like. In addition, polynuclear phenols such as 1-and 2-hydroxynapthalene are also applicable.

In more detail, the novel process of this invention involves admixing molten or liquid phenol with ethylenediamine, a base and glyoxylic acid. The base may be present in aqueous solution and may be selected from alkali metal hydroxides, bicarbonates and the like. The base may also be introduced as alkali metal salts of phenol or of glyoxylic acid. Correspondingly, the glyoxylic acid may also be present in an aqueous system. The reaction proceeds at a temperature of from about 45°-80° C. for a period of about 2 to 16 hours, and preferably for 2 to 4 hours at 70° C.-75° C.

With respect to proportions, the molar ratio of phenol, ethylenediamine, base and glyoxylic acid, respectively, range from 3 to 20, 0.5 to 0.55, 0.75 to 1.25, 0.95 to 1.25. The preferred molar ratio is 13:0.5:1:1. 1 In the preferred ratio, it is seen that the non-phenolic components are present in substantially stoichiometric equivalency while the phenol is present in substantial excess in order to accomplish its dual role.

When small amounts of water are introduced (as occurs by formation of two moles of water during the reaction), and when small amounts of water are included at the outset, it has been found that 2-6% water directs to >95% and 9-13% water content corresponds to 85-95% ortho isomer. Correspondingly larger contamination by water is to be avoided, and the desired range is 5-13% (maximum) water.

While it is possible to isolate the free acid form by precipitating the acid from aqueous solutions at a pH level of 3.0-4.0, there is a corresponding loss of yield in the recovered product. Accordingly, it is preferred that chelation be accomplished by means of an in-situ technique. Thus, the reaction mixture is diluted with water and extracted with an organic solvent to remove the excess phenol. An iron salt is then added to the free acid solution at a pH level of 7.0-8.0 whereupon the resulting deep red solution is dried. Typical iron salts include ferric sulfate, ferric chloride, ferrous chloride, and the like. The iron salts will generally be utilized in excess molar amounts ranging up to about a 25% excess, based on the free acid, in order to achieve quantitative yields.

The following examples will further illustrate the embodiment of this invention. In these examples, all parts given are by weight unless otherwise noted.

EXAMPLE I

This example illustrates the preparation of ethylenebis-(α-imino-o-hydroxyphenylacetic acid) as well as the iron chelate thereof by means of the novel process of this invention.

A reaction vessel fitted with a condenser, dropping funnels and means for mechanical agitation was charged with 367 parts (3.9 moles) of molten phenol. The phenol was retained at a temperature of 40°-45° C. Thereafter, 9.02 parts (0.15 mole) of ethylenediamine were added over a ten minute period and 18 parts (0.23 mole) of an aqueous 50%, by weight, sodium hydroxide solution were added over a subsequent ten minute period. The sodium hydroxide was delivered directly into the reaction mixture in order to avoid build-up of sodium phenoxide on the vessel walls. When the addition of sodium hydroxide was complete, the reaction mixture was cooled to 40°-45° C. and 44.4 parts (0.3 mole) of 50%, by weight, aqueous glyoxylic acid was added dropwise over a fifteen minute period, maintaining a temperature of 40°-45° C. When the addition was complete, the reaction mixture was heated to 70°-75° C. for 2 hours.

The reaction mixture was then diluted with 600 ml. of water and 1000 ml. of carbon tetrachloride. The mixture was stirred vigorously, the layers separated, and the aqueous layer re-extracted twice more with 700 and 500 ml. portions of carbon tetrachloride. The organic layer was removed and the aqueous layer containing the product was weighed and assayed. It was determined that the product yield was 61.4% and that the product contained approximately 95% of the ortho isomer.

A ferric chloride solution containing 35 parts of ferric chloride in 200 ml. of water was then slowly added to the free acid solution with stirring. During chelation, the pH was monitored and maintained between 7.0-8.0 by the addition of 50% sodium hydroxide. When the FeCl₃ addition was complete, the deep red solution was stirred at room temperature for thirty minutes, maintaining a pH of 7.0-8.0. The solution was then evaporated yielding 96 parts of iron chelate.

EXAMPLE II

The free acid procedure outlined in Example I, hereinabove, was repeated utilizing the reaction conditions noted in the following table

| Molar Ratio (Phenol/EDA/50% NaOH/ 50% glyoxylic Acid) | Reaction Temp. (° C.) | Reaction Time(Hrs.) | Yield (%) |
| --- | --- | --- | --- |
| 13/0.5/0.6/1.0 | 70–75 | 2 | 54.5 |
| 13/0.5/0.65/1.0 | 70–75 | 2 | 58.6 |
| 13/0.5/0.7/1.0 | 70–75 | 2 | 60.0 |
| 13/0.5/0.75/1.0 | 70–75 | 2 | 62.3 |
| 12/0.5/0.8/1.0 | 70–75 | 2 | 64.7 |
| 13/0.5/1.5/1.0 | 70–75 | 2 | 54.6 |
| 13/0.5/2.0/1.0 | 70–75 | 2 | 52.8 |
| 13/0.4/1.0/1.0 | 70–75 | 2 | 53.3 |
| 13/0.5/0.7/0.9 | 70–75 | 2 | 59.7 |
| 13/0.5/0.7/0.8 | 70–75 | 2 | 51.3 |
| 8/0.5/2.0/1.0 | 55–60 | 2.5 | 52.8 |
| 10/0.5/1.0/1.0 | 45–50 | 2.5 | 58.0 |
| 10/0.5/1.0/1.0 | 70–75 | 2 | 62.4 |
| 10/0.5/1.0/1.0 | 80–85 | 2 | 56.6 |
| 10/0.5/1.0/1.0 | 80–85 | 3 | 55.7 |

EXAMPLE III

The total procedure described in Example I was repeated under identical conditions achieving the following chelate results.

| Iron Salt | Molar Excess (%) | Free Acid Yield (%) | Iron Chelate Yield (%) | Active Iron (%) |
| --- | --- | --- | --- | --- |
| $FeCl_3$ | 2 | 64.2 | 58.3 | 5.41 |
| $FeCl_3$ | 17 | 61.2 | 61.0 | 5.74 |
| $FeCl_3$ | 27 | 61.5 | 61.1 | 5.47 |
| $FeCl_3$ | 17 | 57.4 | 57.6 | 5.22 |
| $FeCl_3$ | 17 | 63.0 | 63.0 | 5.88 |
| $FeCl_3$ | 17 | 65.1 | 67.6 | 6.09 |
| $FeCl_3$ | 17 | 66.5 | 68.6 | 6.03 |
| $FeCl_2$ | 23 | 59.2 | 58.3 | 5.76 |
| $FeCl_2$ | 23 | 60.1 | 62.3 | 5.85 |
| $FeCl_2$ | 23 | 60.8 | 61.4 | 5.79 |
| $FeCl_2$ | 23 | 64.4 | 59.8 | 5.79 |
| $FeCl_2$ | 23 | 63.6 | 60.9 | 5.78 |

EXAMPLE IV

This example illustrates the advantages resulting from the dual use of phenol as reactant and sole solvent.

The procedure of Example 7 of U.S. Pat. No. 2,824,128 was repeated resulting in the recovery of a 42.0% yield of free acid. This procedure involved the use of a methanol solvent. Analysis by nuclear magnetic resonance spectroscopy revealed the sample to be a mixture of 20.8% ortho isomer and 79.2% para isomer. When treated with $FeCl_3$, the sample formed a red iron chelate which was completely water soluble at a pH of 7. However, at a pH of both 8 and 9, an insoluble form of iron precipitated from the solution.

In contrast, when the procedure as described in Example I, hereinabove, was followed, a yield of 45.1% free acid, by weight, was obtained. NMR analysis revealed a mixture of 88.6% ortho isomer and 11.4% para isomer. When treated with $FeCl_3$, the sample formed a red iron chelate, remaining completely water soluble over a pH range of 7 to 9.

It is thus seen that the instant process yields a much higher percentage of the desired ortho isomer, which in turn allows for the formation of an iron chelate stable under basic pH conditions.

EXAMPLE V

A reaction vessel was charged with 141 parts p-cresol (1.3 moles) and 3 parts ethylenediamine (0.05 moles). Thereafter, 8 parts 50% sodium hydroxide (0.1 moles) and 15.5 parts glyoxylic acid (47.8% by wt., 0.1 moles) were charged at 45°–50° C. The reaction was stirred two hours at 70°–75° C.

The excess p-cresol was extracted and the aqueous phase treated with an aqueous solution containing 12.1 parts ferric chloride as described in Example I. The resulting solution was evaporated to yield 29.7 parts iron chelate, a yield of 64.2%.

Summarizing, it is seen that this invention provides an improved process for the preparation of increased amounts of the ortho isomers of phenolic ethylenediamine-polycarboxylic acids. Variations may be made in proportions, procedures and materials without departing from the scope of the invention as defined by the following claims.

What is claimed is:

1. A process for the preparation of ethylene-bis($\alpha$-imino-hydroxyphenylacetic acid) wherein a major portion thereof is an orto isomeric form, said process comprising reacting, at a temperature of from about 45° to 80° C., phenol with ethylenediamine, glyoxylic acid and a base; said phenol, ethylenediamine, glyoxylic acid and base being present in a molar ratio of 3 to 20, 0.5 to b 0.55, 0.95 to 1.25 and 0.75 to 1.25.

2. The process of claim 1, wherein said molar ratio is 13:0.5:1:1.

3. The process of claim 1, wherein said reaction is conducted at a temperature of 70°–75° C. for a period of two to four hours.

4. The process of claim 1, wherein greater than about 85% of said product is in the ortho isomeric form.

* * * * *